(12) United States Patent
Cichon

(10) Patent No.: US 8,795,684 B2
(45) Date of Patent: Aug. 5, 2014

(54) AGENT FOR USE IN THE TOPICAL OR LOCAL TREATMENT OF CERVICAL DYSPLASIAS

(75) Inventor: Guenter Cichon, Berlin (DE)

(73) Assignee: Charite-Universitaetsmedizin Berlin, Berlin (DE)

( * ) Notice: Subject to any disclaimer, the term of this patent is extended or adjusted under 35 U.S.C. 154(b) by 0 days.

(21) Appl. No.: 13/641,560

(22) PCT Filed: Apr. 15, 2011

(86) PCT No.: PCT/DE2011/075075
§ 371 (c)(1),
(2), (4) Date: Oct. 16, 2012

(87) PCT Pub. No.: WO2011/127924
PCT Pub. Date: Oct. 20, 2011

(65) Prior Publication Data
US 2013/0034584 A1 Feb. 7, 2013

(30) Foreign Application Priority Data
Apr. 16, 2010 (DE) ...................... 10 2010 016 475.5

(51) Int. Cl.
*A61K 45/06* (2006.01)
*C07K 14/005* (2006.01)
*A61K 39/12* (2006.01)
*A61K 39/00* (2006.01)

(52) U.S. Cl.
CPC ..... *A61K 39/0011* (2013.01); *A61K 2039/5256* (2013.01); *A61K 2039/541* (2013.01); *A61K 2039/5254* (2013.01); *C12N 2710/10043* (2013.01); *C12N 2710/20022* (2013.01); *A61K 39/12* (2013.01)
USPC ................................... 424/199.1; 435/235.1

(58) Field of Classification Search
None
See application file for complete search history.

(56) References Cited

U.S. PATENT DOCUMENTS

| 7,659,071 B2 * | 2/2010 | Sastry et al. .................. 435/6.14 |
| 2006/0171949 A1 | 8/2006 | Epstein et al. |
| 2007/0098719 A1 | 5/2007 | Smith et al. |

FOREIGN PATENT DOCUMENTS

| DE | 102004039875 A1 | 3/2006 | |
| DE | WO2009/106362 A1 * | 9/2009 | ........... C07K 14/025 |
| WO | 2008/138648 A1 | 11/2008 | |
| WO | 2009/106362 A1 | 9/2009 | |

OTHER PUBLICATIONS

Gambotto et al. (Cancer Gene Therapy, 1999, vol. 6, p. 45-53).*
Steinwaerder D S et al.: "Human Papilloma Virus E6 and E7 Proteins Support DNA Replication Ofadenoviruses Deleted for the EIA and E1B Genes", in: Molecular Therapy., vol. 4, No. 3, Sep. 2001, pp. 211-216.
Rudin C M et al: "An attenuated adenovirus 0NYX-015 as mouthwash therapy for premalignant oral dysplasia", in: Journal of Clinical Oncology, vol. 21, No. 24, Dec. 15, 2003, pp. 4546-4552.

(Continued)

*Primary Examiner* — Agnieszka Boesen
(74) *Attorney, Agent, or Firm* — Joyce von Natzmer; Agris & von Natzmer LLP

(57) ABSTRACT

The invention relates to an agent for treating cervical dysplasias, comprising a recombinant, genetically modified E1-deleted adenovirus replication defective in non-HPV infected cells, which is suitable for local external application in the region of the portio and the cervix uteri.

10 Claims, 7 Drawing Sheets

(56) References Cited

OTHER PUBLICATIONS

Figure 1:
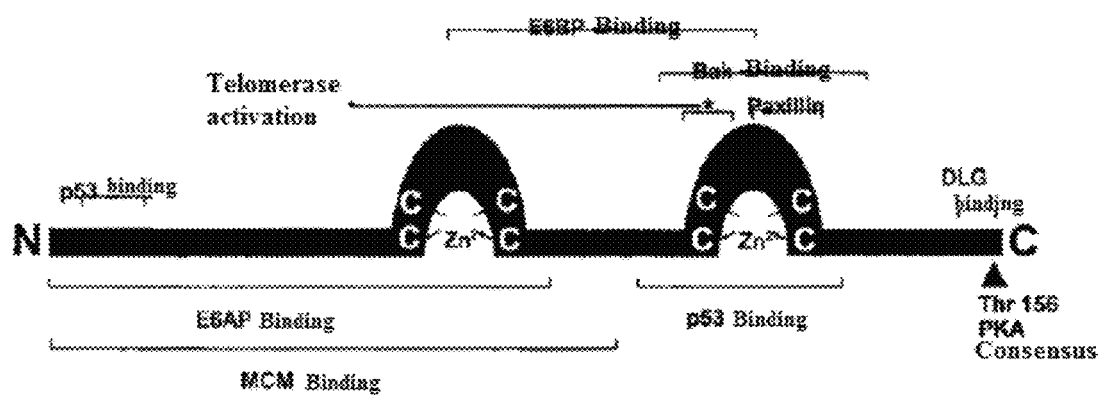

Hoffmann et al: "Combining T-cell Vaccination and Application of Agonistic Anti-GITR mAb (DTA-1) Induces Complete Eradication of HPV Oncogene Expressing Tumors in Mice" in : Journal Immunotherapy, vol. 33, No. 2, Feb./Mar. 2010, pp. 136-145.

Yang et al., "Cellular immunity to viral antigens limits E1-deleted adenoviruses for gene therapy," in Proc. Natl. Acad. Sci., vol. 91, May 1994, pp. 4407-4411.

McGrory et al., "Short communications," in Virology, vol. 163, 1988, pp. 614-617.

Oehlschlaeger et al., "An improved rearranged Human Papillomavirus Type 16 E1 DNA vaccine candidate (HPV-16 E7SH) induces an E7 wildtype-specific T cell response," in Baccine, vol. 24, 2006, pp. 2880-2893.

Schwieger et al., "ras oncogene expression determines sensitivity for intercellular induction of apoptosis," in Carcinogenesis, vol. 22 (9), 2001, pp. 1385-1392.

Loddenkemper et al., "Regulatory (FOXP3+) T cells as target for immune therapy of cervical intraepithelial neoplasia and cervical cancer," in Cancer Science, vol. 100(6), Jun. 2009, pp. 1112-1117.

* cited by examiner

Fig. 2

DNA Sequence (p14):

```
atggactcta cgcttcggtt gtgcgtacaa agcacacacg tagacattcg
tactttggtc gaccaattaa atgacagctc agaggaggag gatgaaatag
atggtccagc tggacaagca gaaccggaca gagcccatta caatattgta
acctttgggc ccatgcatgg agatacacct acattgcatg aatatatgtt
agatttgcaa ccagagacaa ctgatcaatt gaagtgtgaa gctagaattg
agctagtagt agaaagctca gcagacgacc ttcgagcatt cagatctcaa
ttaagcgact cagaggaaga aaacgatgaa atagatggag ttaatcatca
acatttacca gcccgacgag ccgaaccaca acgtcacaca atgttggcta
gcatgcatgg acctaaggca acattgcaag acattgtatt gcatttagag
cctcaaaatg aaattccggt tgacggtacc aagcaaagac atctggacaa
aaagcaaaga ttccataata taaggggtcg gtggaccggt cgatcggat
taaagttta ttctaaaatt agtgagtata gacattattg ttatagtttg
tatggaacaa cattagaaca gcaatacaac aaaccgttgt gtgatttgtt
aattaggcct aggaagcaac agttactgcg acgtgaggta tatgactttg
cttttcggga tttatgcata gtatatagag atgggaatcc atatgctgta
ccgcggccac aggagcgacc cagaaagtta ccacagttat gcacagagct
gcaaacaact atacatgata taatattaga atcgcgaaat gaaaaacgac
gattccacaa aatagctggg cactatagag gccagtcga gatagatttt
tattctagaa ttagagaatt aagacattat tcagactctg tgtatggaga
cacattagaa aaactaacta acactgggtt atacaattta ttaataagga
ctagtaagac agtattggaa cttacagagg tatttgaatt tgcattcaaa
gatttatttg tggtgtatag agacagtata ccgcatgctg cacacgtgcc
aacacggcga ccctacaagc tactgatct gtgcacggaa ctgaacactt
cactgcaaga catagaaata accttaagc tgatccacg tcactattgt
atactctata ttatactcta tgttatactc tgtaatccta ctcaataa
```

Fig. 3

Amino acid sequence (p14):

Met Asp Ser Thr Leu Arg Leu Cys Val Gln Ser Thr His
Val Asp Ile Arg Thr Leu Val Asp Gln Leu Asn Asp Ser
Ser Glu Glu Glu Asp Glu Ile Asp Gly Pro Ala Gly Gln
Ala Glu Pro Asp Arg Ala His Tyr Asn Ile Val Thr Phe
Gly Pro Met His Gly Asp Thr Pro Thr Leu His Glu Tyr
Met Leu Asp Leu Gln Pro Glu Thr Thr Asp Gln Leu Lys
Cys Glu Ala Arg Ile Glu Leu Val Val Glu Ser Ser Ala
Asp Asp Leu Arg Ala Phe Arg Phe Gln Leu Ser Asp Ser
Glu Glu Glu Asn Asp Glu Ile Asp Gly Val Asn His Gln
His Leu Pro Ala Arg Arg Ala Glu Pro Gln Arg His Thr
Met Leu Ala Ser Met His Gly Pro Lys Ala Thr Leu Gln
Asp Ile Val Leu His Leu Glu Pro Gln Asn Glu Ile Pro
Val Asp Gly Thr Lys Gln Arg His Leu Asp Lys Lys Gln
Arg Phe His Asn Ile Arg Gly Arg Trp Thr Gly Arg Ser
Gly Leu Lys Phe Tyr Ser Lys Ile Ser Glu Tyr Arg His
Tyr Cys Tyr Ser Leu Tyr Gly Thr Thr Leu Glu Gln Gln
Tyr Asn Lys Pro Leu Cys Asp Leu Leu Ile Arg Pro Arg
Lys Gln Gln Leu Leu Arg Arg Glu Val Tyr Asp Phe Ala
Phe Arg Asp Leu Cys Ile Val Tyr Arg Asp Gly Asn Pro
Tyr Ala Val Pro Arg Pro Gln Glu Arg Pro Arg Lys Leu
Pro Gln Leu Cys Thr Glu Leu Gln Thr Thr Ile His Asp
Ile Ile Leu Glu Ser Arg Asn Glu Lys Arg Arg Phe His
Lys Ile Ala Gly His Tyr Arg Gly Gln Leu Glu Ile Asp
Phe Tyr Ser Arg Ile Arg Glu Leu Arg His Tyr Ser Asp
Ser Val Tyr Gly Asp Thr Leu Glu Lys Leu Thr Asn Thr
Gly Leu Tyr Asn Leu Leu Ile Arg Thr Ser Lys Thr Val
Leu Glu Leu Thr Glu Val Phe Glu Phe Ala Phe Lys Asp
Leu Phe Val Val Tyr Arg Asp Ser Ile Pro His Ala Ala
His Val Pro Thr Arg Arg Pro Tyr Lys Leu Pro Asp Leu
Cys Thr Glu Leu Asn Thr Ser Leu Gln Asp Ile Glu Ile
Thr Leu Lys Leu Ile Pro Arg His Tyr Cys Ile Leu Tyr
Ile Ile Leu Tyr Val Ile Leu Cys Asn Pro Thr Gln

SEQUENCE LISTING

<160> NUMBER OF SEQ ID NOS: 16

<210> SEQ ID NO 1
<211> LENGTH: 1248
<212> TYPE: DNA
<213> ORGANISM: Artificial Sequence
<220> FEATURE:
<223> OTHER INFORMATION: Human papilloma virus (HPV)

<400> SEQUENCE: 1

```
atggactcta cgcttcggtt gtgcgtacaa agcacacacg tagacattcg tactttggtc      60
gaccaattaa atgacagctc agaggaggag gatgaaatag atggtccagc tggacaagca     120
gaaccggaca gagcccatta caatattgta acctttgggc ccatgcatgg agatacacct     180
acattgcatg aatatatgtt agatttgcaa ccagagacaa ctgatcaatt gaagtgtgaa     240
gctagaattg agctagtagt agaaagctca gcagacgacc ttcgagcatt cagatctcaa     300
ttaagcgact cagaggaaga aaacgatgaa atagatggag ttaatcatca acatttacca     360
gcccgacgag ccgaaccaca acgtcacaca atgttggcta gcatgcatgg acctaaggca     420
acattgcaag acattgtatt gcatttagag cctcaaaatg aaattccggt tgacggtacc     480
aagcaaagac atctggacaa aaagcaaaga ttccataata taagggtcg gtggaccggt      540 cgatccggat taaagttta ttctaaaatt agtgagtata gacattattg ttatagtttg       600
tatggaacaa cattagaaca gcaatacaac aaaccgttgt gtgatttgtt aattaggcct     660
aggaagcaac agttactgcg acgtgaggta tatgactttg cttttcggga tttatgcata     720
gtatatagag atgggaatcc atatgctgta ccgcggccac aggagcgacc cagaaagtta     780
ccacagttat gcacagagct gcaaacaact atacatgata taatattaga atcgcgaaat     840
```

-continued

```
gaaaaacgac gattccacaa aatagctggg cactatagag gccagctcga gatagatttt    900
tattctagaa ttagagaatt aagacattat tcagactctg tgtatggaga cacattagaa    960
aaactaacta acactgggtt atacaattta ttaataagga ctagtaagac agtattggaa   1020
cttacagagg tatttgaatt tgcattcaaa gatttatttg tggtgtatag agacagtata   1080
ccgcatgctg cacacgtgcc aacacggcga ccctacaagc tacctgatct gtgcacggaa   1140
ctgaacactt cactgcaaga catagaaata acccttaagc tgatcccacg tcactattgt   1200
atactctata ttatactcta tgttatactc tgtaatccta ctcaataa               1248
```

<210> SEQ ID NO 2
<211> LENGTH: 415
<212> TYPE: PRT
<213> ORGANISM: Artificial Sequence
<220> FEATURE:
<223> OTHER INFORMATION: Human papilloma virus (HPV)

<400> SEQUENCE: 2

```
Met Asp Ser Thr Leu Arg Leu Cys Val Gln Ser Thr His Val Asp Ile
1               5                   10                  15

Arg Thr Leu Val Asp Gln Leu Asn Asp Ser Ser Glu Glu Glu Asp Glu
            20                  25                  30

Ile Asp Gly Pro Ala Gly Gln Ala Glu Pro Asp Arg Ala His Tyr Asn
        35                  40                  45

Ile Val Thr Phe Gly Pro Met His Gly Asp Thr Pro Thr Leu His Glu
    50                  55                  60

Tyr Met Leu Asp Leu Gln Pro Glu Thr Thr Asp Gln Leu Lys Cys Glu
65                  70                  75                  80

Ala Arg Ile Glu Leu Val Val Glu Ser Ser Ala Asp Asp Leu Arg Ala
                85                  90                  95

Phe Arg Phe Gln Leu Ser Asp Ser Glu Glu Glu Asn Asp Glu Ile Asp
            100                 105                 110

Gly Val Asn His Gln His Leu Pro Ala Arg Arg Ala Glu Pro Gln Arg
        115                 120                 125

His Thr Met Leu Ala Ser Met His Gly Pro Lys Ala Thr Leu Gln Asp
    130                 135                 140

Ile Val Leu His Leu Glu Pro Gln Asn Glu Ile Pro Val Asp Gly Thr
145                 150                 155                 160

Lys Gln Arg His Leu Asp Lys Lys Gln Arg Phe His Asn Ile Arg Gly
                165                 170                 175

Arg Trp Thr Gly Arg Ser Gly Leu Lys Phe Tyr Ser Lys Ile Ser Glu
            180                 185                 190

Tyr Arg His Tyr Cys Tyr Ser Leu Tyr Gly Thr Thr Leu Glu Gln Gln
        195                 200                 205

Tyr Asn Lys Pro Leu Cys Asp Leu Leu Ile Arg Pro Arg Lys Gln Gln
    210                 215                 220

Leu Leu Arg Arg Glu Val Tyr Asp Phe Ala Phe Arg Asp Leu Cys Ile
225                 230                 235                 240

Val Tyr Arg Asp Gly Asn Pro Tyr Ala Val Pro Arg Pro Gln Glu Arg
                245                 250                 255

Pro Arg Lys Leu Pro Gln Leu Cys Thr Glu Leu Gln Thr Thr Ile His
            260                 265                 270

Asp Ile Ile Leu Glu Ser Arg Asn Glu Lys Arg Phe His Lys Ile
        275                 280                 285

Ala Gly His Tyr Arg Gly Gln Leu Glu Ile Asp Phe Tyr Ser Arg Ile
```

```
                    290                 295                 300

Arg Glu Leu Arg His Tyr Ser Asp Ser Val Tyr Gly Asp Thr Leu Glu
305                 310                 315                 320

Lys Leu Thr Asn Thr Gly Leu Tyr Asn Leu Leu Ile Arg Thr Ser Lys
                    325                 330                 335

Thr Val Leu Glu Leu Thr Glu Val Phe Glu Phe Ala Phe Lys Asp Leu
                    340                 345                 350

Phe Val Val Tyr Arg Asp Ser Ile Pro His Ala Ala His Val Pro Thr
                    355                 360                 365

Arg Arg Pro Tyr Lys Leu Pro Asp Leu Cys Thr Glu Leu Asn Thr Ser
                    370                 375                 380

Leu Gln Asp Ile Glu Ile Thr Leu Lys Leu Ile Pro Arg His Tyr Cys
385                 390                 395                 400

Ile Leu Tyr Ile Ile Leu Tyr Val Ile Leu Cys Asn Pro Thr Gln
                    405                 410                 415

<210> SEQ ID NO 3
<211> LENGTH: 21
<212> TYPE: PRT
<213> ORGANISM: Artificial Sequence
<220> FEATURE:
<223> OTHER INFORMATION: Amino Acid 1-21 of HPV16 E7

<400> SEQUENCE: 3

Met His Gly Asp Thr Pro Thr Leu His Glu Tyr Met Leu Asp Leu Gln
1               5                   10                  15

Pro Glu Thr Thr Asp
            20

<210> SEQ ID NO 4
<211> LENGTH: 31
<212> TYPE: PRT
<213> ORGANISM: Artificial Sequence
<220> FEATURE:
<223> OTHER INFORMATION: Amino Acid 27-57 of HPV16 E7

<400> SEQUENCE: 4

Gln Leu Asn Asp Ser Ser Glu Glu Glu Asp Glu Ile Asp Gly Pro Ala
1               5                   10                  15

Gly Gln Ala Glu Pro Asp Arg Ala His Tyr Asn Ile Val Thr Phe
            20                  25                  30

<210> SEQ ID NO 5
<211> LENGTH: 18
<212> TYPE: PRT
<213> ORGANISM: Artificial Sequence
<220> FEATURE:
<223> OTHER INFORMATION: Amino Acid 62-79 of HPV16 E7

<400> SEQUENCE: 5

Asp Ser Thr Leu Arg Leu Cys Val Gln Ser Thr His Val Asp Ile Arg
1               5                   10                  15

Thr Leu

<210> SEQ ID NO 6
<211> LENGTH: 24
<212> TYPE: PRT
<213> ORGANISM: Artificial Sequence
<220> FEATURE:
<223> OTHER INFORMATION: Amino Acid 1-24 of HPV18 E7

<400> SEQUENCE: 6
```

```
Met His Gly Pro Lys Ala Thr Leu Gln Asp Ile Val Leu His Leu Glu
1               5                   10                  15

Pro Gln Asn Glu Ile Pro Val Asp
            20

<210> SEQ ID NO 7
<211> LENGTH: 33
<212> TYPE: PRT
<213> ORGANISM: Artificial Sequence
<220> FEATURE:
<223> OTHER INFORMATION: Amino Acid 30-62 of HPV18 E7

<400> SEQUENCE: 7

Gln Leu Ser Asp Ser Glu Glu Glu Asn Asp Glu Ile Asp Gly Val Asn
1               5                   10                  15

His Gln His Leu Pro Ala Arg Arg Ala Glu Pro Gln Arg His Thr Met
            20                  25                  30

Leu

<210> SEQ ID NO 8
<211> LENGTH: 20
<212> TYPE: PRT
<213> ORGANISM: Artificial Sequence
<220> FEATURE:
<223> OTHER INFORMATION: Amino Acids 67-86 of HPV18 E7

<400> SEQUENCE: 8

Lys Cys Glu Ala Arg Ile Glu Leu Val Val Glu Ser Ser Ala Asp Asp
1               5                   10                  15

Leu Arg Ala Phe
            20

<210> SEQ ID NO 9
<211> LENGTH: 25
<212> TYPE: PRT
<213> ORGANISM: Artificial Sequence
<220> FEATURE:
<223> OTHER INFORMATION: Amino Acid 12-36 of HPV18 E7

<400> SEQUENCE: 9

Pro Gln Glu Arg Pro Arg Lys Leu Pro Gln Leu Cys Thr Glu Leu Gln
1               5                   10                  15

Thr Thr Ile His Asp Ile Ile Leu Glu
            20                  25

<210> SEQ ID NO 10
<211> LENGTH: 29
<212> TYPE: PRT
<213> ORGANISM: Artificial Sequence
<220> FEATURE:
<223> OTHER INFORMATION: Amino Acid 41-69 of HPV18 E7

<400> SEQUENCE: 10

Lys Gln Gln Leu Leu Arg Arg Glu Val Tyr Asp Phe Ala Phe Arg Asp
1               5                   10                  15

Leu Cys Ile Val Tyr Arg Asp Gly Asn Pro Tyr Ala Val
            20                  25

<210> SEQ ID NO 11
<211> LENGTH: 36
<212> TYPE: PRT
<213> ORGANISM: Artificial Sequence
<220> FEATURE:
```

<223> OTHER INFORMATION: Amino Acid 74-109 of HPV18 E7

<400> SEQUENCE: 11

Leu Lys Phe Tyr Ser Lys Ile Ser Glu Tyr Arg His Tyr Cys Tyr Ser
1               5                   10                  15

Leu Tyr Gly Thr Thr Leu Glu Gln Gln Tyr Asn Lys Pro Leu Cys Asp
                20                  25                  30

Leu Leu Ile Arg
            35

<210> SEQ ID NO 12
<211> LENGTH: 21
<212> TYPE: PRT
<213> ORGANISM: Artificial Sequence
<220> FEATURE:
<223> OTHER INFORMATION: Amino Acid 122-142 of HPV18 E7

<400> SEQUENCE: 12

Lys Gln Arg His Leu Asp Lys Lys Gln Arg Phe His Asn Ile Arg Gly
1               5                   10                  15

Arg Trp Thr Gly Arg
            20

<210> SEQ ID NO 13
<211> LENGTH: 25
<212> TYPE: PRT
<213> ORGANISM: Artificial Sequence
<220> FEATURE:
<223> OTHER INFORMATION: Amino Acid 7-31 of HPV18 E7

<400> SEQUENCE: 13

Pro Thr Arg Arg Pro Tyr Lys Leu Pro Asp Leu Cys Thr Glu Leu Asn
1               5                   10                  15

Thr Ser Leu Gln Asp Ile Glu Ile Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Amino Acid 36-64 of HPV18 E7

<400> SEQUENCE: 14

Lys Thr Val Leu Glu Leu Thr Glu Val Phe Glu Phe Ala Phe Lys Asp
1               5                   10                  15

Leu Phe Val Val Tyr Arg Asp Ser Ile Pro His Ala Ala
            20                  25

<210> SEQ ID NO 15
<211> LENGTH: 36
<212> TYPE: PRT
<213> ORGANISM: Artificial Sequence
<220> FEATURE:
<223> OTHER INFORMATION: Amino Acid of 69-104 of HPV18 E7

<400> SEQUENCE: 15

Ile Asp Phe Tyr Ser Arg Ile Arg Glu Leu Arg His Tyr Ser Asp Ser
1               5                   10                  15

Val Tyr Gly Asp Thr Leu Glu Lys Leu Thr Asn Thr Gly Leu Tyr Asn
                20                  25                  30

Leu Leu Ile Arg
            35

```
<210> SEQ ID NO 16
<211> LENGTH: 16
<212> TYPE: PRT
<213> ORGANISM: Artificial Sequence
<220> FEATURE:
<223> OTHER INFORMATION: Amino Acid 122-137 of HPV18 E7

<400> SEQUENCE: 16

Asn Glu Lys Arg Arg Phe His Lys Ile Ala Gly His Tyr Arg Gly Gln
1               5                   10                  15
```

AGENT FOR USE IN THE TOPICAL OR LOCAL TREATMENT OF CERVICAL DYSPLASIAS

CROSS-REFERENCE TO RELATED APPLICATIONS

This is the U.S. national stage of International application PCT/DE2011/075075, filed Apr. 15, 2011 designating the United States and claims priority to DE 10 2010 016 475.5, filed Apr. 16, 2010.

DESCRIPTION

The invention relates to an agent for the local treatment of cervical dysplasia, comprising a recombinant, genetically modified adenovirus replication defective in non-HPV infected cells.

PRIOR ART AND BACKGROUND OF THE INVENTION

The background of the invention relates to diseases that are caused by the human papillomavirus (HPV), in particular cervical cancer and its precursors.

In Germany alone each year about 1 million pathological findings are recorded in women with respect to HPV-induced neoplastic changes in the cervix (cervix uteri). Among a large portion of the women affected, the lesion heals without further measures within the course of a few weeks to months. However, if spontaneous healing does not occur and the development of severe dysplastic epithelial changes takes place, due to the increased risk of a progression to cervical carcinoma the surgical removal of the affected area (conisation) is recommended on the part of the physician. Currently for women with higher grade cervical intraepithelial neoplasia (CIN) there is no therapeutic alternative to the surgical removal of the dysplastic epithelium (conisation). Every year about 150,000 women in Germany have to undergo a conisation. For the women affected, these procedures are not only stressful, but in the case of later pregnancies they also increase the risk of premature birth. The prophylactic inoculation with the newly developed vaccines Gardasil® (Merck) and Cervarix® (GlaxcoSmithKline), also recently introduced in Germany, among young people who have not yet had sexual intercourse reliably prevents a first infection with HPV 6, 11, 16 and 18 (with Gardasil®). However, if a person is already infected with HPV viruses, the vaccine no longer has any affect. Accordingly, its prophylactic effectiveness for preventing cervical intraepithelial neoplasia (CIN lesions) among 25-year old women regardless of the causative HPV serotype is only 17%. Since the first disease peak in the case of cervical carcinoma is between the ages of 35 and 40, even with a broad application of a prophylactic inoculation it will still take about 20 years until the effect of the inoculation has a noticeable influence on the incidence of cervical carcinoma. The necessity of regular screening checkups and the desire for effective, gentler therapeutic measures will continue despite the introduction of the prophylactic inoculation.

The cause of the development of cervical dysplasia is persistent infection are high-risk papillomavirus. Among young women in the age group between 20 and 30 the incidence of high-risk HPV infections is almost 50% (for instance in Denmark). Subsequently, infected women regularly develop cytological symptoms with the so-called cervical smear (pap smear) or dysplastic changes in the sense of a cervical intraepithelial neoplasia (CIN) up to cervical carcinoma. Although the cause of the dysplastic changes is a virus infection, the immunological defensive reaction is often delayed or is inadequate in its effect, so that protracted infections occur that can extend over periods of months to several years. The reason for the inadequate immunological defensive reaction is low replication rates and consequently only low quantities of viral antigens, which reach the target organism and additionally effective HPV mechanisms for suppressing immunological defensive reactions. Since papillomaviruses in particular infect cells of the so-called transformation zone in the region of the cervix uteri, the induced tissue changes are usually limited to the region of the distal channel of the cervix and central portions of the portio uteri.

In the prior art, furthermore, methods can be found for the destruction of HPV oncoprotein expressing cells, which are suitable for the prophylaxis and/or treatment of HPV-induced diseases, such as for instance cervical cancer and its precursors.

Thus WO 2009/106362 A1 describes a selection method for nucleic acids that code for one or more human papillomavirus (HPV) oncoproteins and/or fragments thereof. The object of WO 2009/106362 A1 is to create an allegedly safe vaccine in that it has only antigen sequence motifs, that is, all the other sequence motifs like those with transformation-associated peptide motifs from the DNA of the vaccine were previously removed by cloning measures. A nucleic acid of this type after expression is to be able to induce an immune response in a mammalian organism that leads to the destruction of HPV oncoprotein expressing cells and thus is suitable for the prophylaxis and/or treatment of HPV-induced diseases, such as cervical cancer and its precursors.

Hoffmann et al. (J. Immunother 2010; 33; 136-145) describe a similar approach to the treatment of HPV-induced diseases with a recombinant DNA vaccine, namely an adenovirus based T-cell vaccine in which the problematic sequence motifs were detected, which are to cause a specific T cell response in vivo.

These methods have in common that they relate to vaccination agents, that is, vaccines that directly reach the bloodstream.

OBJECT OF THE INVENTION

Based on this prior art, the object of the present invention is to provide an alternative therapeutic option for treating HPV-induced tissue changes (cervical dysplasia).

DESCRIPTION AND ADVANTAGES OF THE INVENTION

This object is attained by the features of the independent claims; advantageous further measures according to the invention are contained in the other subordinate claims.

The invention is now presented in detail as follows:

According to the invention an agent is provided for the treatment of cervical dysplasia, comprising a recombinant, genetically modified E1-deleted adenovirus that is replication defective in cells not infected with HPV, which is suitable for local external application in the region of the portio and cervix uteri.

It is thereby preferred according to the invention that the E1-deleted adenovirus comprises one or more papillomavirus antigen epitope representing vaccination genes, the expression of which is unsuitable for generating a cellular or humoral immune response against HPV-infected or HPV-oncogene expressing cells.

The invention is based on the surprising finding that the use of the specific interaction between HPV oncogenes and E1-deleted adenoviruses is suitable for a replicating therapeutically useful system in a unique manner for the therapeutic treatment of cervical dysplasia. Since in the cervix there is a direct accessibility of dysplastic cells, it is possible to directly reach oncogene-expressing dysplastic cells and to destroy them by selective replication. In contrast to an injection, here therefore the external local application is particularly preferred. At the same time, the replication of the adenovirus genome in HPV-oncogene expressing cells leads to an increased expression of the vaccination gene and additionally due to the vector-inherent (adenoviral) antigenicity guides the local and systemic immune reactivity to the dysplastic cells, thus at the same time an additional intensification of the systemic, oncogene-specific immune response is induced.

The special feature of the invention is therefore the local application of recombinant adenoviruses in the context of a persistent HPV-infection in the region of the portio and cervix uteri. This is based on the surprising finding that only the local application of recombinant adenoviruses, differentiated from a systemic vaccination, makes it possible to use therapeutically the special biological features in interaction between E1-deleted adenoviruses and HPV-infected or HPV oncogene expressing body cells.

The therapeutic principle of the present invention is based on a synthetic infection of the dysplastic cells of the cervix with a harmless but very immunogenic virus. The fact that the therapeutic virus bears in its genome HPV-specific vaccination genes and due to its own immunogenicity and through the expression of the vaccination genes draws the attention of the immune system to all HPV-infected cells and helps to heal the HPV infection. To these two separately already well-studied therapeutic mechanisms (Yang et al., *Proc Natl Acad Sci USA*. 1994 May 10; 91 (10): 4407-1, Hoffmann et al., *J Immunother.* 2010 February-March; 33 (2): 136-45) is added a third synergistic principle of action, that makes the application of an E1-deleted replication defective adenovirus for the local treatment of HPV oncogene expressing cervical dysplasias a unique principle of action: in a body cell in which the two HPV oncogenes E6 and E7 are expressed, the infection with an E1-deleted adenovirus leads to a selective replication of the adenoviral DNA bearing the vaccination gene. Although this synergistic mechanism is known in principle and has been suggested for the intratumoral application and treatment of cervical carcinomas (Steinwaerder et al., *Mol Ther.* 2001 September; 4 (3): 211-6), it has not hitherto been realized that this principle of action can develop its potential more deeply here due to the different anatomic and infectiological situation of cervical dysplasias compared to solid tumors. The present invention therefore utilizes the biological phenomenon described by Steinwaerder et al (*Mol Ther.* 2001 September; 4 (3): 211-6) for the treatment of persistent HPV infections and early premalignant dysplastic epithelial lesions in the region of the cervix uteri. In contrast to the compact tissue of cervical carcinomas in which all of the cells highly express HPV E6 and E7, the epithelia of the cervix uteri usually comprise only a few cell layers in which only individual disseminated cells express HPV oncogenes. Cervical dysplasias are in particular an areal skin change, which comprises only a few micrometers in its horizontal extent and is restricted to the outermost skin layer, the epithelium.

The synergy between E1-deleted adenovirus and HPV infected epithelial cells, which the invention utilizes, can be described as follows:

The invention is based on the—well-known—finding that recombinant replication defective adenoviruses represent the most effective in vivo gene transfer system of the past 20 years. Adenoviruses have hitherto been used in more than 150 clinical studies as a vector system for the transfer of therapeutic genes or for the expression of vaccination genes. Wild-type adenoviruses are non-enveloped DNA viruses that bear a double stranded DNA about 36,000 base pairs in length and typically produce light infections of the upper respiratory tract. The replication defective E1-deleted recombinant adenoviruses used for therapeutic purposes in medicine are characterized by a deletion of the adenoviral E1 region covering about 3,000 base pairs. These viruses are able to very effectively infect almost every human body cell, but cannot themselves replicate in this cell due to a lack of the E1 gene (E1A and E1B gene). The production of these viruses requires the use of special cell lines that bear the adenoviral E1 gene in their genome and in this manner provide their function indirectly (in trans). Through the deletion of the E1 genes in the adenoviral genome, a "gap" is produced, into which foreign genes (therapeutic genes or vaccination genes) can be cloned and which after the infection of a body cell are expressed there. In order to create additional space for the cloning of larger transgenes, expanded variants of recombinant adenoviruses bear a second deletion in the region of the adenoviral E3 region that permits the cloning of transgenes up to a total length of about 7,800 base pairs. The plasmids that are used for the production of the viruses used within the scope of this invention were developed in the :laboratory of Frank Graham (McMaster University, Hamilton, Ontario, Canada) in the 1980s (McGrory W J et al., *Virology* 1988, 163 (2): 614-7).

Although the functional presence of the adenoviral E1 gene is essential for a high replication and development of new infectious adenoviruses, the function of the adenoviral D1-genes can be complemented by other oncogenes up to a certain extent, which leads to a limited genomic replication of the adenoviral genome in oncogene-expressing cells. Among these oncogenes capable of transactivation, the papilloma viral oncogenes E6 and E7 have a special position, since they can cause a sustained transactivation, which leads to a replication of the adenoviral genome up to several hundred copies per cell. In this manner the expression of the transgene (vaccination gene, therapeutic gene) takes place not only from one or a few copies, but from several hundred copies simultaneously, which dramatically increases the overall strength of the transgene expression.

The invention also utilizes this; a "therapeutic" gene or vaccination gene integrated into the adenovirus genome (as within the scope of this invention) is then expressed not only from a few copies but from several hundred copies. This mechanism in turn leads to a considerable increase in the expression level of the therapeutic gene or vaccination gene and induces at the same time the destruction of the HPV-infected cell due to the overexpression of adenoviral antigens.

Within the collective of HPV infected cells, as a rule only a part of the cells expresses the HPV oncogenes E6 and E7. However, these cells pose the greatest threat of the production of serious dysplasias and later the development of cervical cancer. With a comprehensive direct local external infection of HPV-infected cells of the cervix with an E1-deleted adenovirus according to the invention, however, precisely HPV oncogene-expressing cells of the vaccination gene will express particularly markedly due to the mechanism described above. The increased replication of the adenoviral genome in HPV-oncogene expressing cells thus contributes to the therapeutic effect in two ways. Firstly, the replication leads to an intensification of the T-cell response by increased expression of the vaccination gene and thus the provision of target antigen, and secondly, the continuous replication of the adenoviral genome leads to the destruction of the HPV oncogene expressing cell. In this manner precisely those cells that pose the greatest danger for the development of dysplastic cell changes are selectively destroyed. The invention is therefore based on the finding that neither a systematic application nor a local injection is suitable for ensuring a comprehensive infection of HPV-infected tissue. To the contrary, even each local bleeding—such as is caused by an injection—should be avoided in order to prevent a contact of the "therapeutic" viruses according to the invention with neutralizing antibodies. According to the invention, therefore, only an external application makes it possible to infect completely the dysplastic lesions including their original tissue in the region of the transformation zone and the distal cylindrical epithelium.

In the later infection phase of HPV-infected body cells an increased expression of the two HPV oncogenes E6 and E7 occurs. The expression of these two oncogenes leads to an acceleration of the cell cycle with simultaneous inhibition of cellular tumor-suppressor genes (in particular p53 and pRb). The expression of these two HPV oncogenes is the cause of the development of dysplastic epithelial defects of the cervix uteri and ultimately responsible for the development of cervical cancer. The cancellation of the expression inhibition of the HPV oncogenes therefore represents a decisive pathomechanism of dysplasia development.

The expression of the two HPV oncogenes E6 and E7 is decisive for the pathogenesis of cervical dysplasia. These oncogenes stimulate the cell cycle of the infected cells in a varied and unphysiological manner. If in this situation an HPV-oncogene expressing cell is infected with an E1-deleted adenovirus, however, the beginning replication of the adenoviral genome and the overexpression of the transgenes leads to a slow overload of the infected cell with adenoviral or transgene expression products and drives the dysplastic cell selectively to cell death. At the same time, the replication mechanism also induces an increase in the expression level of the vaccination gene and the induced immune response.

Since the adenovirus used within the scope of this invention bears a vaccination gene, the expression of which is able to induce a specific immune response against HPV oncogenes, the infection of an E6/E7 expressing cell via the replication mechanism described above leads to an additional intensification of the vaccination gene expression and thus to a further increase of the cellular immunity to HPV oncogene expressing cells.

However, in principle the described functional synergy between HPV-E6/E7 oncogenes and E1-deleted adenoviruses is independent of the nature of the transgene so that this principle also could be used for the over expression of other therapeutic transgenes.

The invention thus opens up a completely new kind of therapeutic approach to the treatment of cervical dysplasia. A local external application of the agent according to the invention, containing recombinant E1-deleted adenoviruses in the region of the portio and the cervix uteri leads to a successful treatment of HPV-induced local tissue changes.

The invention therefore manages without a surgical procedure on the patient, which naturally is a considerable advantage over comparable methods since it ensures the physical integrity of the patient.

According to the invention it is preferred that recombinant adenoviruses are used, which code for one or more vaccination genes or immunomodulatory genes, the expression of which in turn is suitable for generating a cellular or humoral immune response against HPV-infected or HPV oncogene expressing cells which or are suitable for generating an intensified immune response against HPV-infected cells. Vaccination genes are preferred that cause an immune response against the human papillomavirus (HPV) 16, 18, 25, 31, 33, 35, 39, 45, 51, 52, 53, 56, 58, 59, 66, 68, 73 or 82. Those vaccination genes are particularly preferred thereby that cause an immune response against the human papillomaviruses HPV 16 and HPV 18.

On the one hand an intensified expression of the coding transgenes and thus an intensified immunological effect is associated with the active replication of therapeutic adenoviruses in HPV oncogene expressing cells, and on the other hand the active replication of the therapeutic virus in HPV E6/E7 expressing cells leads to an intensified local release of therapeutic viruses in regions in which they are most urgently needed from a therapeutic point of view.

The advantageous therapeutic effect provided by the invention with an external application of E1-deleted recombinant adenoviruses applied in the region of the portio and the cervix uteri is composed of several components:

The infection of a mammalian cell with an E1-deleted adenovirus regularly leads to a specific activation of the cellular immune system, which entails an inactivation or elimination of the adenovirus-infected cell. A local infection of the dysplastic epithelium with recombinant adenoviruses due to this mechanism will already lead to a partial elimination of dysplastic cells. Since the epithelia in the region of dysplastic lesions are regularly infected with high-risk papillomaviruses, an increased release of HPV antigens is also associated with an adenovirus-mediated destruction of these cells. The destruction and phagocytosis of HPV-infected cells also leads regularly to an intensified presentation of papilloma viral antigens and thus to an intensified immune reaction against HPV infected cells.

Unlike an HPV-infected cell, the infection of a (not infected) cell with a replication deficient adenovirus therefore always reliably leads to a reaction of the cellular immune system, as a result of which the infected cell is inactivated or destroyed. This generally undesirable reaction makes the utilization of recombinant adenoviruses as a transport vehicle (vector) for therapeutic genes for the permanent correction of monogenetic diseases virtually impossible.

With the treatment according to the invention of cervical dysplasia, however, the high antigenicity is precisely desired, since it can compensate for the lack of antigenicity of HPV-infected cells and forces a defense reaction of the immune system. The invention utilizes this in that it develops this mechanism within the scope of a local direct external infection of the cells. A use of this type of recombinant adenoviruses for the local treatment of dysplastic changes of the cervix uteri has not hitherto taken place.

Since antibodies against serotype 5 adenoviruses can be verified among the majority of young adults, the local external adenovirus infection according to the invention in the region of the portio and cervix uteri represents an application method that is largely independent of the infection inhibiting effects of neutralizing antibodies, since through the good accessibility of the epithelia secreted antibodies before a therapeutic infection can be more easily removed. Only an external application of the adenoviruses used within the scope of the invention makes it possible to comprehensively infect the dysplastic lesions including their original tissue in the region of the transformation zone and the distal cylindrical epithelium.

The invention is therefore based on treating the HPV-infected tissue externally with the agent according to the invention, which leads to an infection of the HPV-infected tissue with recombinant E1-deleted adenoviruses, which can replicate in HPV E6/E7 expressing cells (like the infected tissue).

However, these can multiply only and exclusively in this infected tissue, since such cells have a lack of antigenicity and thus cause a targeted immune response.

In a special embodiment of the invention it is provided within the scope of a local therapy of cervical dysplasias to use recombinant E1-deleted adenoviruses that bear at least one or two vaccination genes. These vaccination genes represent important papillomavirus antigenic epitopes. After the infection of a cell with a recombinant adenovirus, these genes are strongly expressed and in a short time a papillomavirus antigen pool is produced which can exceed the antigen quantity produced within the scope of an HPV wild-type infection. In this manner the expression of these genes in the context of an adenovirus infection forces a specific cellular immune response against papillomavirus oncogenes and papillomavirus envelope proteins. It has been possible to show the effectiveness of this measure on HPV oncogene expression mouse tumor models.

Vaccination genes are used here, in particular the vaccination gene "p14," the fundamental production of which is described in WO 2009/106362 A1 (there: Example 1 "Cloning of a recombinant therapeutic vaccination gene without transformation associated peptide motifs") as well as in Hoffmann et al. (J. Immunother 2010; 33: 136-145). Reference is made thereto and to the entire disclosure of WO 2009/106362 A1 and Hoffmann et al. (J. Immunother 2010; 33: 136-145) and this is incorporated into the present application as reference in their entirety.

The recombinant vaccination gene (p14) described there is characterized in that all potentially pathogenic and transforming sequence sections have been eliminated. An analysis of the T cell epitope still coded in the recombinant vaccination gene p14 (based on the 4 most frequent MCH-1 molecules in the Caucasian population) shows that despite the elimination of all potentially pathogenic and transforming sequence sections, almost 70% of the high-affinity T cell epitopes are still coded by the vaccination gene. Furthermore, with respect to the recombinant vaccination gene (p14) by means of transformation assays for the exclusion of a transforming residual activity still remaining in the vaccination gene it was possible to show that the stable expression of the vaccination gene p14 (pCMV-p14) in NIH-3T3 in contrast to the wild-type oncogene no longer shows any transforming residual activity.

As evidence of the ability of the vaccination gene after expression in mammals to develop a specific immune response directed against HPV oncogenes, $1 \times 10^6$ C3 tumor cells were transplanted in mice (C57BL6) by subcutaneous injection. C3 tumor cells express the HPV oncogenes E6 and E7. 7 days after the tumor transplant, the mice were administered once with a dose of $1 \times 10^{10}$ infectious particles (i.p) in 200 µl injection buffer in an intramuscular manner. In all 10 of the mice treated in this manner a complete and permanent healing of the tumors occurred, whereas the tumors in the control group (after the application of a control virus (Ad-lacZ) in 9 out of 10 cases continued to grow (cf. WO 2009/106362 A1 and Hoffmann et al., J. Immunother 2010; 33: 136-145). It was therefore possible to show that the expression of the recombinant vaccination gene after one-time adenoviral gene transfer (intramuscular application 7 days after tumor transplant) in mammals (C57BL6 mice) triggers a T cell response that is sufficient to completely and permanently destroy already grown C3 tumors. In all 10 tumor-bearing test animals, the one-time vaccination with Ad-p14 led to the permanent destruction of the tumors, while in 9 of 10 test animals in the control group (application of Ad-lacZ) the tumors continued to grow unhindered after virus application.

This vaccination gene has surprisingly proven to be particularly effective with respect to the present invention.

The present invention therefore utilizes this finding that E1-deleted adenoviruses can replicate in HPV E6/E7 expressing cells and thus support the destruction of HPV-infected epithelia in a targeted manner. In this manner an intensified and targeted destruction of HPV-infected cells occurs, which bear an increased risk of a dysplasia development and at the same time an intensified expression of the vaccination genes and thus an intensified immune response is connected to the replication.

The vaccination gene preferably used is one that was produced by the fusion of fragments of the HPV oncogenes E6 and E7 of the high-risk HPV 16 and HPV 18 (short name: "p14"). In this respect the corresponding DNA sequence (1248 bp, SEQ ID No. 1) of the vaccination gene p14 is also the subject matter of the invention. This vaccination gene p14 codes for a protein with the amino acid sequence according to SEQ ID no. 2 (415 amino acids).

According to the invention it is further preferred that the E1-deleted adenovirus comprises one or more immunomodulatory genes which are suitable for generating an intensified immune response against HPV-infected cells. Interleukins are hereby preferred for immunomodulation, wherein the invention is not restricted to interleukins, but likewise comprises all usual immunomodulators with the same action. Inflammatory interleukins, such as for example IL1, IL-2 or IL-12, are particularly preferred.

The advantage of the invention lies in that the local destruction of HPV-infected cells due to the local treatment with recombinant adenoviruses leads to an intensified release of papilloma viral antigens and thus the defensive reaction against viral antigens is promoted.

The optimal development and the optimal interaction of the described mechanisms for the treatment of cervical dysplasias requires the application of a method that minimizes the influence of blood constant neutralizing antibodies against adenoviruses. This is possible only through the local external application of recombinant E1-deleted adenoviruses in the region of the portio and cervix uteri, since here, due to the good accessibility, a conditioning of the local epithelium preceding the local infection is possible and in this manner secreted antibodies are removed and optimal local infection rates are ensured.

The subject matter of the invention is also a pharmaceutical composition or a medication for application in humans for the local treatment of cervical dysplasias, comprising a recombinant genetically modified adenovirus that is replication defective in cells not infected with HPV.

The invention therefore provides a therapeutically active agent, in particular a pharmaceutically active composition, which is suitable as a medication for the local external application of HPV-induced local tissue changes, in particular for the local external application in the region of the portio and the cervix uteri, comprising recombinant replication-defective E1-deleted adenoviruses. In a preferred embodiment, these also comprise vaccination genes representing one more papillomavirus antigen epitopes, the expression of which is suitable for generating a cellular or humoral immune response against HPV-infected or HPV oncogene expressing cells. A corresponding pharmaceutical composition comprising the agent according to the invention has the necessary galenic additives that are suitable for the preparation and administration of the medication for the external local application in the region of the portio and cervix uteri.

The agent according to the invention can be administered alone or combined with at least one other pharmaceutically active substance, for example another pharmaceutically active nucleic acid, for example an inflammatory interleukin and/or a costimulatory molecule. Examples of costimulatory molecules are described in US 2006/0171949, the disclosure of which is explicitly referenced hereby. In a particularly preferred embodiment, the molecule is an activator of the GITR signal path, in particular an agonistic antibody binding to the GITR receptor or a soluble form of the GITR ligand (GITR-L). Examples of corresponding GITR binding molecules are described in US 2007/0098719, the disclosure of which is explicitly referenced hereby. Furthermore, the vaccine according to the invention can also be administered together with adjuvants, such as bacterial toxins, e.g. cholera toxin or heat-stable *E. coli* enterotoxin, chemical adjuvants or with cytokines, e.g., with GM-CCF.

For understanding and for the field of application of the invention, the anatomy of the female uterus is necessary: the uterus is composed of two sections: the body of the uterus (corpus uteri) with the uterine cavity (cavum uteri) and the cervix (cervix uteri) with the cervical portio (portio vaginalis, usually referred to merely as portio). The cervix usually covers approximately the lower third of the uterus, which in anatomical terms is a thick-walled muscular hollow organ, and projects as the cervical portio (portio vaginalis) into the upper part of the vagina. The cervix is composed of connective tissue and musculature and in the longitudinal direction has a cavity, the cervical canal. This is lined with a mucous membrane, the glands of which form a tough mucus. The function of the mucus is to close the uterine cavity to the outside and thus to protect it from germs from the vagina. The mucous membrane, which lines the cervix in the region of the cervical os, is flatter than the mucous membrane in the interior of the uterus. There it is similar to normal mucous membrane, such as occurs, for instance in the oral cavity (squamous epithelium).

As already stated several times, the present invention is used for the local external application in the region of the portio and the cervix uteri, that is, for the treatment of the mucous membrane there. In this respect a classic inoculation is ruled out and therefore suspensions, gels, ointments, lotions or other essentially liquid application forms like solutions of all kinds in a variety of grades of viscosity are preferred. However, essentially all application forms and galenic compositions are preferred that are suitable for application to the mucous membrane.

The following description relates to the manner in which the viruses according to the invention are combined with chiefly conventional pharmaceutically harmless carriers, whereby dosage forms are achieved, which are suitable for the different administration methods that are used for a given patient, and the disease, disorder or condition for which a given patient is treated. A pharmaceutical composition of this type according to the invention comprises one or more of the viruses described above, together with a pharmaceutically harmless carrier according to the properties and the expected behavior of such carriers well known to the person skilled in the art.

The use of a medication for external application onto the mucous membrane in the region of the portio and the cervix uteri is therefore also claimed within the scope of the invention. The medication is suitable for penetrating into the uppermost epithelial layers. In this respect, the use of recombinant, genetically modified E1-deleted adenoviruses replication-defective in cells not infected with HPV for the production of a medication for local external application in the region of the portio and cervix uteri with human patients is preferred, wherein the medication is designed for administration in a target dose of in the range of $1\times10^8$ to $1\times10^{12}$ infectious particles (abbreviation: i.p.) over a period of at least 3 days, namely on day 0, on date 3 and on day 30.

The use is particularly preferred of a target dose of $1\times10^{10}$ infectious particles (i.p.). However due to individual factors, dosage adjustments can also be conceivable, which fall below or exceed the given target dose by up to two orders of magnitude ($1\times10^8$-$1\times10^{12}$ infectious particles).

The quantity of viruses which can be combined with the carrier materials in order thus to form an individual dosage form depends on the treated patient and the respective administration method. However, it is dear that a specific dosage and treatment plan for a specific patient depends on a variety of factors, including the effectiveness of the respectively used compound, the age, body weight, general state of health, sex, nutrition, time of administration, rate of excretion, the drug combination and the discretion of the treating physician as well as the severity of the respectively treated disease. The active substance quantity can also depend on the therapeutic agent or prophylactic that is possibly jointly administered with the active ingredient.

In the present context, the term "carrier" comprises harmless extenders, excipients, auxiliaries, constituents, solution aids, viscosity-modifying agents, preservatives and other agents that are well known to the person skilled in the art in order to give the final pharmaceutical composition favorable properties.

In particular the carrier used with the pharmaceutical compositions according to the invention comprises different classes and types of additives, which are selected independently from the groups cited essentially in the sections below.

Antimicrobial agents, including agents against bacteria, fungi and protozoa, are added if the pharmaceutical composition is applied topically to areas of the skin which were probably exposed to a harmful environment, or have suffered abrasions or cuts that make the skin susceptible to an infection by bacteria, fungi or protozoa. Antimicrobial preservatives are added to the pharmaceutical compositions according to the invention in order to protect them against the growth of possibly harmful microorganisms, which usually migrate in the aqueous phase, but in some cases can also grow in the oil phase of a composition. Therefore preservatives are desired which are soluble in aqueous media as well as in lipids.

For topical application, the pharmaceutical compositions can be formulated as a suitable ointment that contains the active constituent suspended or dissolved in one or more carriers. However, the pharmaceutical compositions can also be formulated as a suitable lotion or cream that contain the active constituents suspended or dissolved in one or more pharmaceutically harmless carriers.

Dermatological active substances are often added to the pharmaceutical compositions according to the invention where they are to be applied topically. Dispersion agents and suspending agents are used as auxiliaries in the production of stable formulations. Emollients are preferably non-oily, water-soluble substances, which soften and calm the skin, particularly skin that has become dry due to excessive water loss. Substances of this type are used with pharmaceutical compositions according to the invention that are intended for topical application. Emulsifiers, including emulsifying and thickening agents and emulsion auxiliaries, are used for the production of oil-in-water emulsions when they form the basis of the pharmaceutical compositions according to the invention. If the pharmaceutical composition according to the invention is to be applied topically, penetrants can be used. Thickeners are typically used with formulations for topical application in order to give them the desired viscosity or the desired handling properties. Sugars are often used in order to give the pharmaceutical compositions according to the invention different desired properties and in order to improve the results obtained.

The production of the pharmaceutical compositions according to the invention is carried out in an extremely simple manner, as is well known to one with average skill in the art. If the pharmaceutical compositions according to the invention are simple aqueous solutions or solutions in other solvents, the different constituents of the total composition are added in any practical order, which is determined mainly by reasons of convenience. Those constituents that have a poor solubility in water, but sufficient solubility in the same auxiliary solvent with water, can all be dissolved in this auxiliary solvent, after which the water content of the carrier is added to the auxiliary solvent, whereby the substances dissolved therein dissolve in water. To support this dispersion operation or solution operation, a surfactant can be used.

In a further preferred embodiment of the invention the agent is therefore present in the form of a solution, emulsion, suspension, ointment, a balm, oil, gel, foam, in liquid form, as a thermoreversible gel (to be used in liquid form), in the form of a tampon containing the active substance and/or in the form of a cream. It was completely surprising that the advantages of the agent according to the invention could be improved again in that it is inserted into the cited galenic forms. The person skilled in the art is familiar with other formulation concepts for the introduction of the agent according to the invention into carrier substances such as, e.g., emulsions or other products for dermal application, such as, e.g., liquid forms that can preferably be anhydrous or aqueous, wherein the aqueous ones according to the invention can be differentiated in single-phase systems or multiple-phase systems. Furthermore, semi-solid forms, which can be anhydrous or aqueous, can be used, wherein in turn a division into single-phase systems and multiple-phase systems is possible with the aqueous semi-solid forms. Furthermore, solid forms can preferably be used that are lipophilic or hydrophilic. Examples of forms of this type in addition to those cited are e.g., fatty ointments, foams, gel creams, hydrodispersion gels, thin emulsions, lotions, ointments, sprays and creams.

The agent or the pharmaceutical composition according to the invention or the drug resulting therefrom, has a galenic that renders possible the application onto the mucous membranes.

The person skilled in the art is thereby aware of different compositions with respect to the viscosity in low-viscosity and in high-viscosity. Nanoemulsions or oils or oleogels have rather a low viscosity, whereas hydrogels or hydrocreams or O/W emulsions or W/O emulsions have a high viscosity. When liquid application forms are used, as stated above, these can be divided into anhydrous and aqueous systems. In the case of the anhydrous systems, in particular apolar systems, polar systems without emulsifiers and polar systems with emulsifiers are preferred. In the case of the aqueous systems, single-phase systems such as solutions and microemulsions are preferred, in the case of the multiple-phase systems, multiple emulsions, W/O emulsions or O/W emulsions are preferred. Among the solid/liquid systems preferred forms are suspensions or liquid/solid/liquid systems and suspension/emulsion systems. The person skilled in the art is familiar with various options for preparing pharmaceutical carriers of this type. With the O/W emulsions, preferred galenic conducting substances are O/W emulsifiers, W/O emulsifiers, liquid hydrophilic constituents and liquid lipophilic constituents. With the W/O emulsions, preferred galenic conducting substances are W/O emulsifiers, O/W emulsifiers, liquid and semi-solid lipophilic constituents, gelatinizing agents, liquid hydrophilic constituents and/or salts.

Particularly advantageously nanotransport systems with dendritic architecture can be used, as are disclosed in DE 10 2004 039 875. This is incorporated into the disclosure of the present teaching according to the application. Various transport systems are known from the prior art, such as liposomes, polymeric micelles, polymer conjugates or simple dendritic core-shell architectures. Polymeric micelles are physical aggregates of ambiphilic macromolecules, which can form spontaneously in water by self-organization. Usually the inner block is nonpolar or ionic and the outer block, which protects the core by steric stabilization, is polar. They are often used for the solubilization of nonpolar ingredients or ingredient combinations with limited solubility in water or for the transport of oligonucleotides. Such dermal transport systems can advantageously be used in order to render possible a quick passage of the agent according to the invention into tumors.

Nanotransport systems with simple dendritic core-shell architecture likewise render possible targeted active substance transports. In contrast to physical aggregates of ambiphilic molecules, due to the covalent modification of dendritic macromolecules with corresponding shell, stable micelle-like structures can be obtained, which are suitable for the encapsulation of drugs. Particularly advantageously nanotransport systems can be used, which are composed at least of one dendritic core and at least two shells. Preferably, the shells have different polarities, thus a polarity gradient is achieved, around which nonpolar as well as polar active substances or combinations of active substances can be enclosed. The advantageous nanotransport systems therefore advantageously have a multi-shell unimolecular structure. Due to the combination of the different shells, it is easily possible to repeatedly create new nanotransport systems adapted to the active substance and the use thereof. For a nanotransport system of this type dendrimers as well as hyperbranched polymers can be used. Thus the use of hyperbranched polymers is thus also advantageous, whereby advantageously the synthesis expense as well as the costs can be reduced. In a preferred embodiment the above-referenced dendritic core is composed of polyglycerol, polyamide, polyamine, polyether or polyester. These compounds can also be further modified within the dendritic architecture. The dendritic core can thus be polarized according to its modification. It was completely surprising that agents of this type can be used particularly well in the application through the skin. They are approx. four times as well suited to apply particles into the skin as other lipid nanoparticles.

A further subject of the invention also relates to applicators according to the invention, which, avoiding bleeding, are preferred for the administration of the agent according to the invention or the pharmaceutical composition or the drug. An applicator is particularly preferred hereby comprising an injection device, which, while avoiding a local bleeding, is suitable for penetrating into the uppermost epithelial layers. In order to improve the local introduction of virus into the epithelium of the portio, such applicators are therefore preferred which have a modified surface structure, for example, bear tiny tips, which however are so short that they punch only small holes into the epithelium, without causing bleeding.

Figure 4:
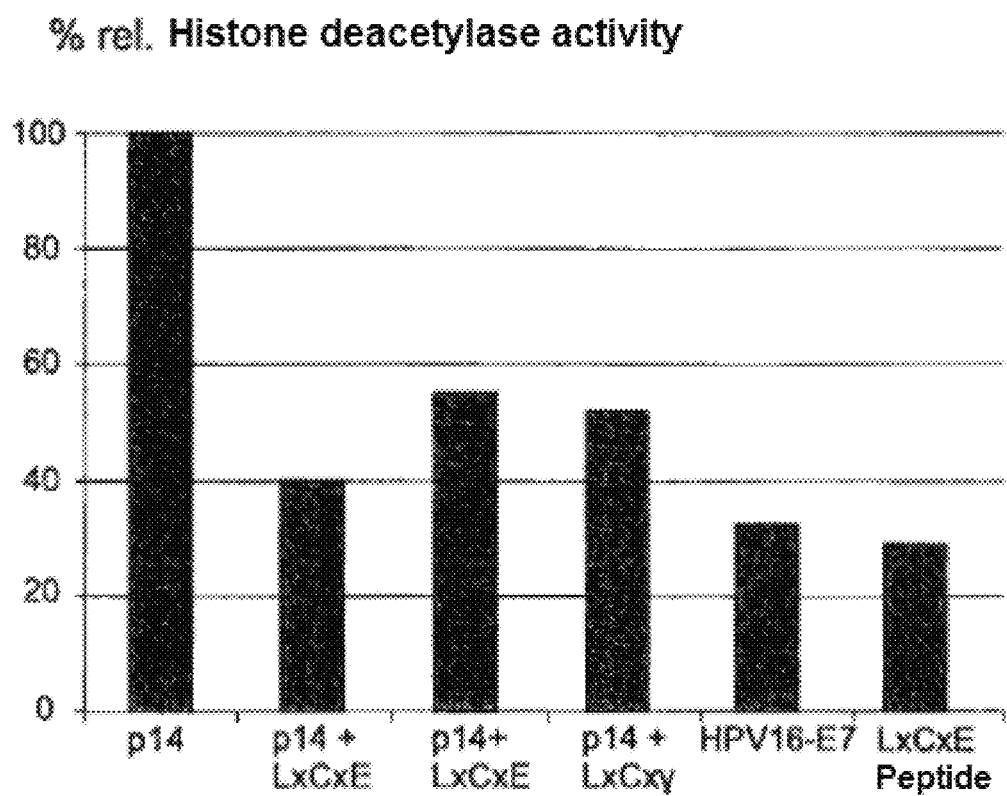
Figure 5:
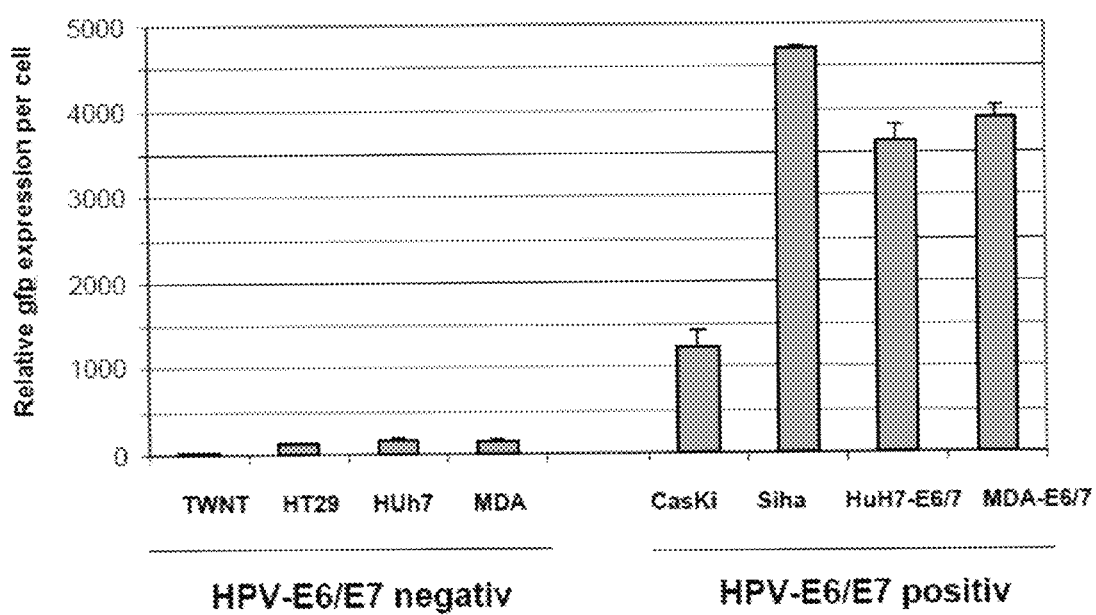
Figure 6:
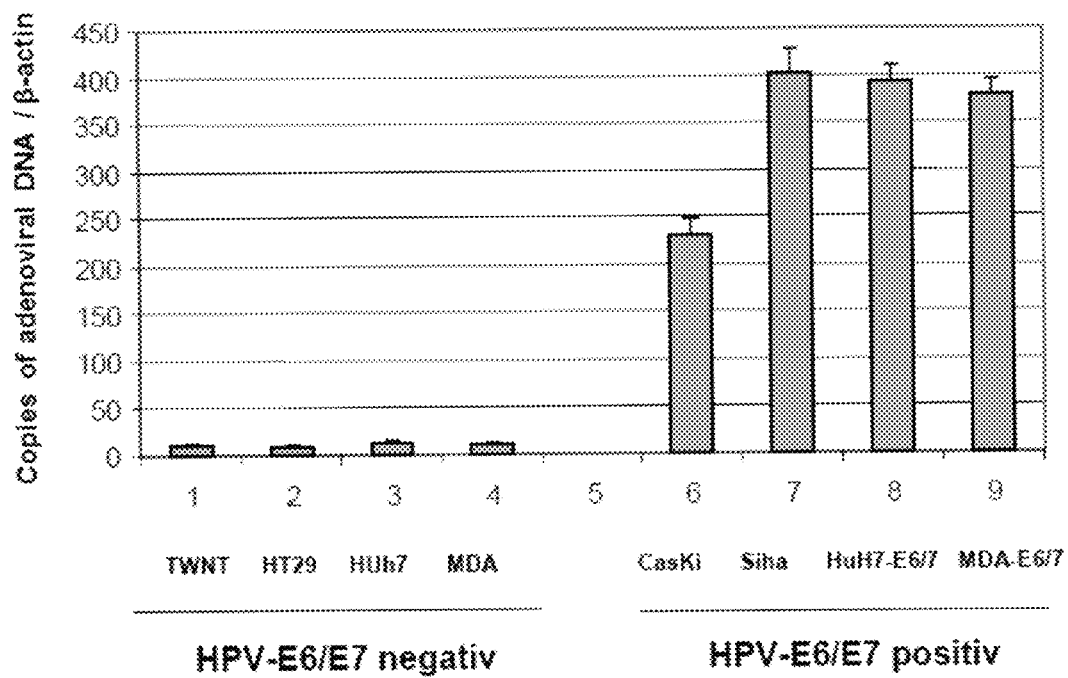

The invention is now described in more detail based on examples and figures, without being limited thereto; they show:

FIG. 1 diagrammatically, the protein binding domains (function domains) present in the oncoprotein HPV18-E6, and the localization thereof;

FIG. 2 nucleic acid sequence of the vaccination gene p14;

FIG. 3 amino acid sequence of the vaccination gene p14;

FIG. 4 the precipitation of LxCxE bearing GSTp14 fusion constructs after incubation with core extracts;

FIG. 5 image to prove the functional synergism of HPV oncogenes expressing cells and E1-deleted adenoviruses by measuring the reporter gene expression in HPV oncogene positive and HPV oncogene negative cells after adenoviral gene transfer of a reporter gene (measuring the strength of the relative gfp expression per cell after infection with Ad-gfp);

FIG. 6 image to prove the functional synergism of HPV oncogene expressing cells and E1-deleted adenoviruses by measuring the adenoviral genome copies in HPV oncogene positive and HPV oncogene negative cells after adenoviral gene transfer of a reporter gene (measurement of the copies of adenoviral DNA/β-actin).

Figure 7:
Figure 7A:
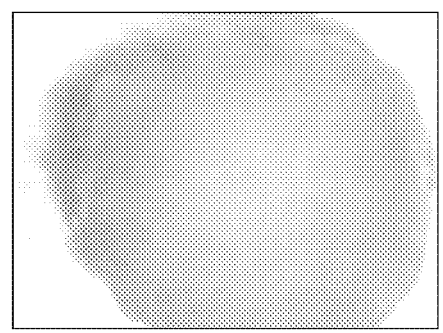

FIGS. 7, 7a direct proof of the infectability of human cervical canal epithelia with a reporter gene bearing adenovirus (Ad-lacZ).

EXEMPLARY EMBODIMENTS

1. Vaccination Gene

The vaccination gene corresponds to that which has already been described in WO 2009/106362 (there Example 1: "Cloning a recombinant therapeutic vaccination gene without transformation-associated peptide motifs") and in Hoffmann et al. (J. Immunother 2010; 33: 136-145). Reference is made thereto and to the entire disclosure of WO 2009/106362 and Hoffmann et al. (J. Immunother 2010; 33: 136-145) and incorporated as reference into the present application.

The vaccination gene (p14) was cloned by fusion of 14 fragments of the two HPV oncogenes E6 and E7 of the high risk HPV 16 and HPV 18 and is able to induce a cellular immunity against oncogenes of the serotypes HPV16 and HPV18, as well as sequence-related further HPV serotypes. It no longer has any transforming properties. The vaccination gene was cloned into an E1-deleted adenovirus and its therapeutic potential was tested in mice. The one-time intramuscular application of Ad-p14 in mice (C57BL6) in a dose of 1×10e10 i.p. induces an immune response that not only reliably prevents the growth of HPV oncogene expressing tumor cells, but also heals already established tumors reliably and permanently.

In Detail:

1a. Identification of Transformation-Associated Peptide Motifs in HPV Oncoproteins.

A protein coded by an oncogene often conveys its oncogenic effect in that it binds to endogenous cellular proteins and influences them in their physiological effect or brings them to a quick degradation.

The cellular proteins concerned are usually molecules that play an important role in the control of the cell cycle. The interaction between oncogene and cell cycle protein takes place via short peptide motifs often having only a few amino acids. Table 1 shows the most important protein binding motifs of HPV16 E6 and E7 oncogenes, which have been identified by deletion studies.

TABLE 1

Sequence motifs of HPV16-E6 and E7 that are involved in imparting transforming properties ("AS" stands for amino acid).

| Protein motif | Function | Literature |
|---|---|---|
| AS Position In E6 HPV16 | | |
| -MFQ-  8-10 | Degradation of p53 | Klingelhutz A J et al. *Nature* 1996; 380 (6569): 79-82 Huibregtse J M et al. *Mol Cell Biol.* 1993; 13 (8): 4918-4927 |
| -CxxC-  37-40 / 70-73 / 110-113 / 43-146 | Formation of two zinc finger formations | Kanda T et al., *Virology.* 1991; 182 (2): 723-731 Sherman L et al. *J Virol* 1996; 70 (5): 3269-3279 |
| -CPEE-  118-121 | Telomerase activation | Klingelhutz A J et al. *Nature*, 1996; 380 (6569): 79-82 |
| -RRETQL(V)-  153-158 | Binding PDZ domain containing proteins | Kiyono T et al., *Proc Natl Acad Sci USA* 1997; 94 (21): 11612-11616 Brehm A et al. *Nature* 1998; 391 (6667): 597-601 |
| AS-position in E7 HPV16 | | |
| -LxCxE-  22-26 | Mediates Rb binding and activates histone deacetylase, promotes cell proliferation | el Deiry W S et al., *Cell* 1993; 75 (4): 817-825 |
| -CxxC  58-61 / 91-94 | Development of a zinc finger formation | |
| -EDLL-  80-83 | Changes the function of cell cycle protection (p21waf-1, p27Kip1, S4, M2-PK) and stimulates the aerobic glycolysis | Polyak K et al., *Cell* 1994; 78 (1): 59-66 Zwerschke W et al. *Proc Natl Acad Sci USA* 1999; 96 (4): 1291-1296 |

TABLE 1-continued

Sequence motifs of HPV16-E6 and E7 that are involved in imparting transforming properties ("AS" stands for amino acid).

| Protein motif | Function | Literature |
|---|---|---|
| | | Shimizu J et al. *Nat Immunol.* 2002; 3 (2): 135-142 |

FIG. 1 shows diagrammatically the protein binding domains present in oncoprotein HPV18-E6 and the localization thereof In the therapeutic HPV vaccines produced in the past, these protein binding motifs are maintained virtually complete. Even the concept of reorganization of fragments presented by Öhlschläger and colleagues (Öhlschläger P et al., *Vaccine.* 2006; 24 (15): 2880-2893) although it changes the position of the binding motif in the vaccination gene compared to the wild-type oncogene, it does not destroy the integrity of the binding motif. Binding studies with synthetic peptides such as L×C×E (AS 22-26 in HPV16-E7) or the PDZ-domain binding RRETQL on the C terminus of E6 (AS 153-158 in HPV16-E6) document the high affinity of these peptide motifs for cell cycle proteins such as the Rb/histone deacetylase complex or different PDZ-domain-containing tumor suppressor proteins such as MAGl-1 or SAP97/dlg (P. L. Triozzi et al., *J Immunother* 28 (2005), pp 382-38826; B. Klencke et al. *Clin Cancer Res* 8 (2002), pp. 1028-1037; J. Tartaglia et al., *Virology* 188 (1992), pp. 217-232).

1b. Cloning the Vaccination Gene

For the construction of the therapeutic vaccination gene (p14), 14 DNA fragments were selected from HPV16 and HPV18 E6 and E7 oncogenes and mirror image cloned for arrangement in the wild-type genes taking into consideration the correct reading frame. Each of the 14 DNA fragments codes for 21-36 amino acids (Table 2). The adenoviral base vectors and the cloning strategy were used as described in Schwieger et al. (*Carcinogenesis* 2001 September; 22 (9): 1385-9250).

TABLE 2

Sequence fragments of HVP16 and HPV18 E6 and E7 oncogenes, which were selected for cloning the vaccination gene p14

| | | Position in p14 | |
|---|---|---|---|
| Position in HPV16 E7 | | | |
| 1) aa 1-21: | MHGDTPTLHEYMLDLQPETTD | aa 55-75 | (SEQ IN No. 3) |
| 2) aa 27-57: | QLNDSSEEEDEIDGPAGQAEPDRAHYNIVTF | aa 22-52 | (SEQ IN No. 4) |
| 3) aa 62-79: | DSTLRLCVQSTHVDIRTL | aa 2-19 | (SEQ IN No. 5) |
| Position in HPV18 E7 | | | |
| 4) aa 1-24: | MHGPKATLQDIVLHLEPQNEIPVD | aa 135-158 | (SEQ IN No. 6) |
| 5) aa 30-62: | QLSDSEEENDEIDGVNHQHLPARRAEPQRHTML | aa 100-132 | (SEQ IN No. 7) |
| 6) aa 67-86: | KCEARIELVVESSADDLRAF | aa 78-97 | (SEQ IN No. 8) |
| Position in HPV18 E7 | | | |
| 7) aa 12-36: | PQERPRKLPQLCTELQTTIHDIILE | aa 253-277 | (SEQ IN No. 9) |
| 8) aa 41-69: | KQQLLRREVYDFAFRDLCIVYRDGNPYAV | aa 222-250 | (SEQ IN No. 10) |
| 9) aa 74-109: | LKFYSKISEYRHYCYSLYGTTLEQQYNK-PLCDLLIR | aa 184-219 | (SEQ IN No. 11) |
| 10) aa 122-142: | KQRHLDKKQRFHNIRGRWTGR | aa 161-181 | (SEQ IN No. 12) |
| Position in HPV18 E7 | | | |
| 11) aa 7-31: | PTRRPYKLPDLCTELNTSLQDIEIT | aa 367-391 | (SEQ IN No. 13) |
| 12) aa 36-64: | KTVLELTEVFEFAFKDLFVVYRDSIPHAA | aa 336-364 | (SEQ IN No. 14) |
| 13) aa 69-104: | IDFYSRIRELRHYSDSVYGDTLEKLTNT-GLYNLLIR | aa 298-333 | (SEQ IN No. 15) |
| 14) aa 122-137: | NEKRRFHKIAGHYRGQ | aa 280-295 | (SEQ IN No. 16) |

The entire vaccination gene codes for a 415 amino acids (1248 pb). The nucleic acid and amino acid sequence of p14 are shown in FIGS. 2 and 3 (SEQ ID Nos. 1 and 2). The expression takes place under the control of a CMV promoter and a CMV polyadenylation signal. An exclusion of potentially dangerous sequence motifs leads inevitably also to the loss of potential T cell epitopes. With the oncogene fragments selected for cloning the vaccination gene, an attempt was made to keep the loss of therapeutically relevant T cell epitopes low, in that the inserted deletions remained restricted precisely to the extent of the identified binding motifs. An analysis of the vaccination gene produced regarding the number of the remaining T cell epitopes shows that 7 out of 8 of the E6 epitopes of HPV 16 and 18 highly affine to the 4 most frequent MHC class I molecules are still coded in the gene (Table 3.)

TABLE 3

The table shows the presence (1) or absence (0) of the highly affine T cell epitopes of the p14 vaccine with respect to the 4 MHC class I alleles most common in the population. Despite the sequence restrictions carried out for reasons of biological safety, the presented p14 vaccine still codes for all 5 of the highly affine HLA-A0201 epitopes (about 50% of the population bear this MHC class I locus) and beyond the 4 most frequent MHC classes 7 out of 8 of the highly affine epitopes.

|  | HPV16-E6 | HPV18-E6 |
| --- | --- | --- |
| A 0201 | 1-1-1-1-1 (5/5) | 1-1-1-0-0 (3/5) |
| A 2402 | 1-1-0-1-1 (4/5) | 1-0-0-0-1 (2/5) |
| A 0101 | 1-0-1-0-1 (3/5) | 0-1-1-0-0 (2/5) |
| A 0301 | 1-0-0-1-0 (2/5) | 1-0-0-0-1 (2/5) |

The complete neutralization of the transforming potential of the wild-type oncogenes carried out by fragmentation and exclusion of peptide binding motifs was tested in transformation assays (Schwieger et al., *Carcinogenesis* 2001 September; 22 (9): 1385-9250). It was possible to show that the recombinant p14 vaccination gene in contrast to the wild-type oncogenes no longer has any transforming activity (Table 4).

TABLE 4

Compared to the starting constructs, the p14 vector shows no more transforming activity.

| Vector | Colonies | Transfection efficiency (1000 cells) | Transformation frequency |
| --- | --- | --- | --- |
| pCMV-p14 | 0 | 21% | 0% |
| pHPV16E6/E7 | 138 | 19% | 66% |
| pHPV18E6/E7 | 21 | 38% | 5.5% |
| pras | 121 | 39% | 31% |
| pCMVSL (mock) | 0 | 17% | 0% |

FIG. 4 shows that the precipitation of LxCxE bearing GSTp14 fusion constructs after incubation with core extracts leads to a reduction of histone deacetylase activity in the supernatant. The effect is independent of the position of the LxCxE motif within the p14 protein (α, β, γ).

The re-insertion of the LxCxE motif thus gives the expression product an increased affinity to Rb histone deacetylase complexes compared to the p14 starting construct. This effect is relatively position-independent and thus makes it clear what risk is posed by the presence of this or similar binding motifs in the vaccination gene.

A disturbance of the proliferation control is associated with the direct competition between the retinoblastoma tumor-suppressor gene (Rb) and LxCxE, which is connected to an increased proliferation tendency. In this manner it becomes clear that undesirable interactions between vaccines and cellular proteins can be ensured only by consistent elimination of all potentially protein-binding ranges from the vaccine. In the presented vaccination gene p14, all of the sequence motifs of HPV16-E6 and E7 or the sequences corresponding thereto from HPV18-E6 and E7 contained in Table 1 are no longer present. It has been shown that it is nevertheless possible to clone a vaccination gene that has an impressive immunotherapeutic potential and which at the same time ensures a maximum of biological safety. The presented DNA vaccine is the currently safest and at the same time most powerful construct of its type.

2. Intensification of the Expression of Therapeutic Genes by Selective Adenoviral Cell Lines Expressing in HPV Oncogene After the biological safety of the vaccine and its basic suitability for the induction of a specific T cell response directed against HPV oncogenes was tested in earlier experiments, in further tests its suitability as an externally (mucosal) applicable vaccine is to be shown. Furthermore, in particular its ability to replicate in HPV oncogene expressing cells is to be shown. In order to study the mechanism of the support of a genomic replication of E1-deleted adenoviruses by HPV oncogene expressing cells, HPV-E6 and E7 positive cell lines (CasKi, Siha, Huh7-E6/7, MDA-MB468-E6/7) and HPV-negative cell lines (TWNT, HT1080, Huh7, MDA-MB468) were infected with an E1-deleted adenovirus (Ad-gfp) bearing a reporter gene in an MOI (multiplicity of infection) of 10 and the gfp expression per cell determined 48 hours after infection. With comparable transfection efficiency, the gfp expression in HPV oncogene-positive cell lines is higher by a factor of 10-50 than in HPV-negative cell lines (FIG. 5). The infection of a cell expressing HPV-oncogenes (E6 and E7) with an E1-deleted adenovirus (Ad-gfp) leads to a 10-50-fold intensification of the expression of the adenoviral transgene (gfp). The HPV oncogenes are able to activate the adenoviral replication machinery and in this manner increase the number of copies of the adenoviral genomes, whereby the expression strength of the coding transgenes is increased. Therefore proof could be produced of the functional synergism of HPV oncogene expressing cells and E1-deleted adenoviruses by measuring the reporter gene expression in HPV oncogene positive and HPV oncogene negative cells after adenoviral gene transfer of a reporter gene.

The determination of the number of the genomic adenoviral copies based on the number of β-actin copies taking into consideration the transfection efficiency by quantitative PCR shows that there is a linear connection between the expression level and the number of copies present per cell (see FIG. 6). 48 hours after infection of an HPV oncogene positive cell, up to over 400 genomic copies of the adenoviral genome per β-actin copy could be found, while it was possible to verify a maximum of up to 20 copies in HPV negative cells. FIG. 6 therefore shows the number of adenoviral copies 48 hours after infection HPV oncogene positive and HPV oncogene negative cell lines. It is discernible that the infection of an HPV oncogene-expressing cell leads to an activation of the adenoviral replication machinery and in this manner increases the transgene expression.

3. Animal Experiment

An animal experiment to verify a specific T cell activation was carried out, wherein by external, mucosal (sublingual) application of Ad-p14 in mice (C57BL6) based on the specific effect it was possible to prevent the growth of HPV oncogene (HPV16 E6/E7) expressing tumors (C3). In view of the fact that in animals, in particular mice, a local external application in the region of the cervix is out of the question for anatomical and practical aspects, the present experiment is used for the fundamental applicability and functionality of the agent according to the invention.

In this respect the effectiveness of a mucosal vaccination in mice (C57B16) with the HPV oncogene epitope expressing adenovirus Ad-p14 was tested, compared to a control adenovirus (Ad-lacZ) and the addition of buffer alone (mock). This experiment is to be seen in particular with respect to the effectiveness of a mucous membrane application ("mucosal") of the invention. The vaccination already described above by means of an intramuscular injection (cf. also WO 2009/106362 A1 and Hoffmann et al., *J. Immunother* 2010; 33: 136-145) is not to be equated with an applicability in the region of the mucous membrane.

In order to show the fundamental effectiveness of a mucosal application (sublingual), anesthetized mice (C57BL6) were carefully given 20 µl of an Ad-p14-containing virus suspension ($1 \times 10^{10}$ i.p.) with a pipette under the tongue (sublingual). In the control group the same quantity of a control virus (Ad-lacZ) or only buffer (mock) was applied. 10 days later $1 \times 10^6$ C3 tumor cells were applied (injected) subcutaneously under the right flank and the tumor growth was observed. While in the control group (only buffer) all of the treated animals (10/10) showed tumor growth (100%), in the second control group (Ad-lacZ) 9 out of 10 tumors grew (90%). In the group of mice previously treated with Ad-p14, however, a tumor grew only in one of the animals thus treated (10%), which demonstrates the feasibility of a mucosal vaccination (cf. Table 5).

TABLE 5

Number of animals with and without tumor growth

| Mock | 10/10 |
|---|---|
| Ad-lacz | 9/10 |
| Ad-p14 | 1/10 |

The results according to Table 5 clarify the fundamental success of the animal experiment, according to which a tumor growth could be prevented by means of the sublingual application of the agent according to the invention. A prior vaccination with Ad-p14 thus reliably prevents the growth of tumors.

3. Human Experiment

In order to illustrate the infectability of epithelia of the human cervix, a small still vital tissue sample (of an operation preparation after hysterectomy), namely a tissue cylinder 3 mm in diameter of tissue of a human uterus (cervical canal) of a patient was isolated and within 60 minutes after operative removal infected with a recombinant adenovirus (ad-lacZ) bearing a reporter gene in a concentration of $2 \times 10^9$ infectious particles (i.p.)/ml for 30 minutes and subsequently cultivated for 48 hours in gassed culture medium at 37° C.

Subsequently, after brief fixation in Formalin an X-Gal staining to show the intracellular reporter gene activity (expression of the transgene LacZ for β-glactosidase (β-gal) was carried out. The histological image in FIG. 7 shows the good infectability of human cervical epithelia based on the characteristic colorations. This is particularly clear in comparison with a non-transfected control tissue (cf. FIG. 7a), which does not show any lacZ expression.

The invention claimed is:

1. A method for treating cervical dysplasia, comprising externally applying to the portio of the cervix uteri of a human patient diagnosed with or at risk of cervical dysplasia, wherein the portio of the cervix uteri is a part of the cervix projecting into an upper part of the vagina, a recombinant, genetically modified E1-deleted adenovirus comprising one or more genes encoding papillomavirus antigens, in an amount effective to treat cervical dysplasia,
wherein the recombinant, genetically modified E1-deleted adenovirus is replication Defective in non-HPV infected cells and wherein the expression of HPV oncogenes E6 and E7 in HPV infected cells of the human patient results in replication of the recombinant, genetically Modified E1-deleted adenovirus.

2. The method of claim 1, wherein a target dose of the E1-deleted adenoviruses of about $1 \times 10^8$ to $1 \times 10^{12}$ infectious particles (i.p.) is administered over a period of at least 3 days, namely on day 0, on day 3 and on day 30.

3. The method according to claim 2, wherein the target dose is $1 \times 10^{10}$ infectious particles (i.p.).

4. The method according to claim 2, wherein the E1-deleted adenoviruses penetrates into the top epithelial layers.

5. The method of claim 1, wherein expression of the genes encoding papillomavirus antigens cause an immune response against the human papilloma viruses (HPV) 16, 18, 25, 31, 33, 35, 39, 45, 51, 52, 53, 56, 58, 59, 66, 68, 73 or 82.

6. The method of claim 1, wherein at least one of said genes encoding papillomavirus antigens are a fusion of the HPV oncogenes E6 and E7 of high risk HPV 16 and HPV 18.

7. The method of claim 6, wherein one of the genes encoding papillomavirus antigens has the sequence of SEQ ID NO: 1.

8. The method of claim 5, wherein one of the antigens has the sequence of SEQ ID NO: 2.

9. The method according to claim 1, wherein the E1-deleted adenovirus further comprises one or more immunomodulatory genes, which are suitable for generating an intensified immune response against HPV-infected cells.

10. The method according to claim 9, wherein one or more of the immunomodulatory genes is an inflammatory interleukin.

* * * * *

UNITED STATES PATENT AND TRADEMARK OFFICE
CERTIFICATE OF CORRECTION

PATENT NO.      : 8,795,684 B2
APPLICATION NO. : 13/641560
DATED           : August 5, 2014
INVENTOR(S)     : Cichon Page 1 of 1

It is certified that error appears in the above-identified patent and that said Letters Patent is hereby corrected as shown below:

In the Claims

Column 30, lines 28-29, issued claim 8 should appear as follows:
The method of claim 6, wherein one of the antigens has the sequence of SEQ ID NO: 2.

Signed and Sealed this
Second Day of December, 2014

Michelle K. Lee
*Deputy Director of the United States Patent and Trademark Office*